(12) United States Patent
Parish et al.

(10) Patent No.: US 9,180,041 B2
(45) Date of Patent: Nov. 10, 2015

(54) COMPRESSION SEQUENCED THERMAL THERAPY SYSTEM

(71) Applicant: ThermoTek, Inc., Flower Mound, TX (US)

(72) Inventors: Overton L. Parish, Frisco, TX (US); Niran Balachandran, Lewisville, TX (US); Tony Quisenberry, Highland Village, TX (US); Clark R. Havis, Round Rock, TX (US)

(73) Assignee: ThermoTek, Inc., Flower Mound, TX (US)

( * ) Notice: Subject to any disclaimer, the term of this patent is extended or adjusted under 35 U.S.C. 154(b) by 18 days.

(21) Appl. No.: 14/256,504

(22) Filed: Apr. 18, 2014

(65) Prior Publication Data

US 2014/0228717 A1    Aug. 14, 2014

Related U.S. Application Data

(60) Continuation of application No. 12/730,060, filed on Mar. 23, 2010, now Pat. No. 8,753,383, which is a division of application No. 10/894,369, filed on Jul. 19, 2004, now abandoned.

(60) Provisional application No. 60/588,453, filed on Jul. 16, 2004, provisional application No. 60/550,658, filed on Mar. 5, 2004, provisional application No. 60/488,709, filed on Jul. 18, 2003.

(51) Int. Cl.
*A61F 7/00* (2006.01)
*A61F 5/34* (2006.01)
(Continued)

(52) U.S. Cl.
CPC ... *A61F 7/00* (2013.01); *A61F 5/34* (2013.01); *A61F 7/0097* (2013.01); *A61F 7/02* (2013.01); *A61H 1/008* (2013.01); *A61H 9/0078* (2013.01); *A61F 2007/0001* (2013.01); *A61F 2007/0054* (2013.01); *A61F 2007/0076* (2013.01); *A61F 2007/0091* (2013.01); *A61F 2007/0273* (2013.01); *A61F 2007/0296* (2013.01);
(Continued)

(58) Field of Classification Search
CPC ............... A61F 7/00; A61F 7/02; A61F 7/03; A61F 7/08
USPC .................. 607/104, 108–112, 114; 128/898
See application file for complete search history.

(56) References Cited

U.S. PATENT DOCUMENTS 773,828 A    11/1904   Titus
2,110,022 A   3/1938   Kliesrath
(Continued)

FOREIGN PATENT DOCUMENTS

CH        670 541      6/1989
DE      35 22 127      1/1987
(Continued)

OTHER PUBLICATIONS

U.S. Appl. No. 12/364,434, Quisenberry.
(Continued)

*Primary Examiner* — Aaron Roane
(74) *Attorney, Agent, or Firm* — Winstead PC (57) ABSTRACT

A sequential compression and temperature therapy blanket with a plurality of air chambers is disclosed. The air chambers are filled and released by a valve assembly that may be separate from or integrated within the blanket. The temperature therapy blanket includes a fluid bladder for delivering hot and/or cold therapy to a patient. The temperature therapy blanket may also include an air bladder for providing compression.

8 Claims, 8 Drawing Sheets

(51) Int. Cl.
   *A61F 7/02*   (2006.01)
   *A61H 9/00*   (2006.01)
   *A61H 1/00*   (2006.01)

(52) U.S. Cl.
   CPC ... *A61H2201/025* (2013.01); *A61H 2201/0207* (2013.01); *A61H 2201/0214* (2013.01); *A61H 2201/0242* (2013.01); *A61H 2201/0264* (2013.01); *A61H 2201/0285* (2013.01); *A61H 2201/165* (2013.01)

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere Nicoll |
| 3,345,641 A | 10/1967 | Jennings |
| 3,367,319 A | 2/1968 | Carter, Jr. |
| 3,548,809 A | 12/1970 | Conti |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,547,906 A | 10/1985 | Nishida et al. |
| 4,590,925 A | 5/1986 | Dillon |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| 4,738,249 A | 4/1988 | Linman et al. |
| D295,897 S | 5/1988 | Thimm-Kelly |
| 4,741,338 A | 5/1988 | Miyamae |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,969,881 A | 11/1990 | Viesturs |
| 4,979,375 A | 12/1990 | Nathans et al. |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,062,414 A | 11/1991 | Grim |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,496,357 A | 3/1996 | Jensen et al. |
| 5,505,726 A | 4/1996 | Meserol |
| 5,507,792 A | 4/1996 | Mason |
| 5,509,894 A | 4/1996 | Mason et al. |
| 5,514,079 A | 5/1996 | Dillon |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| D380,874 S | 7/1997 | Caswell |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,029 A | 1/1998 | Visco et al. |
| 5,711,155 A | 1/1998 | DeVilbiss et al. |
| D393,073 S | 3/1998 | Downing et al. |
| 5,731,954 A | 3/1998 | Cheon |
| 5,733,321 A | 3/1998 | Brink |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |

(56) References Cited

U.S. PATENT DOCUMENTS

| | | | |
|---|---|---|---|
| 5,795,312 A | 8/1998 | Dye |
| 5,807,294 A | 9/1998 | Cawley et al. |
| 5,827,208 A | 10/1998 | Mason |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,865,841 A | 2/1999 | Kolen et al. |
| 5,871,526 A | 2/1999 | Gibbs et al. |
| 5,890,371 A | 4/1999 | Rajasubramanian et al. |
| 5,901,037 A | 5/1999 | Hamilton et al. |
| 5,923,533 A | 7/1999 | Olson |
| 5,947,914 A | 9/1999 | Augustine |
| 5,980,561 A | 11/1999 | Kolen et al. |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,117,164 A | 9/2000 | Gildersleeve et al. |
| 6,125,036 A | 9/2000 | Kang et al. |
| 6,129,688 A | 10/2000 | Arkans |
| 6,135,116 A | 10/2000 | Vogel et al. |
| 6,176,869 B1 | 1/2001 | Mason et al. |
| 6,186,977 B1 | 2/2001 | Andrews et al. |
| 6,235,049 B1 | 5/2001 | Nazerian |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,443,978 B1 | 9/2002 | Zharov |
| 6,462,949 B1 | 10/2002 | Parish, IV et al. |
| 6,468,237 B1 | 10/2002 | Lina |
| 6,508,831 B1 | 1/2003 | Kushnir |
| D472,322 S | 3/2003 | Hoglund et al. |
| D473,315 S | 4/2003 | Miros et al. |
| D473,656 S | 4/2003 | Miros et al. |
| D473,948 S | 4/2003 | Elkins et al. |
| 6,551,264 B1 | 4/2003 | Cawley et al. |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish, IV et al. |
| 6,936,019 B2 | 8/2005 | Mason |
| D510,140 S | 9/2005 | Brown |
| 6,945,988 B1 | 9/2005 | Jones |
| D510,626 S | 10/2005 | Krahner et al. |
| D515,218 S | 2/2006 | McGuire et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| D551,351 S | 9/2007 | Silva |
| D551,352 S | 9/2007 | Frangi |
| 7,306,568 B2 | 12/2007 | Diana |
| 7,354,411 B2 | 4/2008 | Perry et al. |
| D568,482 S | 5/2008 | Gramza et al. |
| D569,985 S | 5/2008 | Ganapathy et al. |
| 7,427,153 B1 | 9/2008 | Jacobs et al. |
| 7,429,252 B2 | 9/2008 | Sarangapani |
| 7,484,552 B2 | 2/2009 | Pfahnl |
| 7,492,252 B2 | 2/2009 | Maruyama |
| D595,620 S | 7/2009 | Kingsbury |
| D601,707 S | 10/2009 | Chouiller |
| D608,006 S | 1/2010 | Avitable et al. |
| D612,947 S | 3/2010 | Turtzo et al. |
| D613,870 S | 4/2010 | Shust |
| 7,717,869 B2 | 5/2010 | Eischen, Sr. |
| D618,358 S | 6/2010 | Avitable et al. |
| D619,267 S | 7/2010 | Beckwith et al. |
| D620,122 S | 7/2010 | Cotton |
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| D627,896 S | 11/2010 | Matsuo et al. |
| D628,300 S | 11/2010 | Caden |
| D630,759 S | 1/2011 | Matsuo et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,910 B2 | 3/2011 | Schirrmacher et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 7,959,588 B1 | 6/2011 | Wolpa |
| D649,648 S | 11/2011 | Cavalieri et al. |
| 8,052,630 B2 | 11/2011 | Kloecker et al. |
| D655,420 S | 3/2012 | Bowles |
| D655,821 S | 3/2012 | Matsuo |
| D657,063 S | 4/2012 | Chiang |
| D660,438 S | 5/2012 | Kennedy et al. |
| D660,439 S | 5/2012 | Chen et al. |
| D663,850 S | 7/2012 | Joseph |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,444,581 B1 | 5/2013 | Maxon-Maldonado et al. |
| 8,449,483 B2 | 5/2013 | Eddy |
| 8,485,995 B1 | 7/2013 | Maxon-Maldonado |
| 8,753,300 B2 | 6/2014 | Deshpande |
| 8,753,383 B2 | 6/2014 | Parish et al. |
| 8,827,935 B2 | 9/2014 | Maxon-Maldonado |
| 8,834,393 B2 | 9/2014 | Maxon-Maldonado et al. |
| 2001/0039439 A1 | 11/2001 | Elkins et al. |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0127215 A1 | 7/2003 | Parish, IV et al. |
| 2003/0135252 A1 | 7/2003 | MacHold et al. |
| 2003/0163183 A1 | 8/2003 | Carson |

(56) References Cited

U.S. PATENT DOCUMENTS

| | | |
|---|---|---|
| 2003/0171703 A1 | 9/2003 | Grim et al. |
| 2003/0176822 A1 | 9/2003 | Morgenlander |
| 2003/0191437 A1 | 10/2003 | Knighton et al. |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0133214 A1 | 6/2005 | Pfahnl |
| 2005/0177093 A1 | 8/2005 | Barry et al. |
| 2005/0182364 A1 | 8/2005 | Burchman |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0116620 A1 | 6/2006 | Oyaski |
| 2006/0241549 A1 | 10/2006 | Sunnen |
| 2006/0276845 A1 | 12/2006 | George et al. |
| 2006/0282028 A1 | 12/2006 | Howard et al. |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0082029 A1 | 4/2008 | Diana |
| 2008/0103422 A1 | 5/2008 | Perry et al. |
| 2008/0132816 A1 | 6/2008 | Kane et al. |
| 2008/0132976 A1 | 6/2008 | Kane et al. |
| 2008/0249559 A1 | 10/2008 | Brown et al. |
| 2008/0262399 A1 | 10/2008 | Kovelman et al. |
| 2008/0319362 A1 | 12/2008 | Joseph |
| 2009/0069731 A1 | 3/2009 | Parish et al. |
| 2009/0109622 A1 | 4/2009 | Parish et al. |
| 2009/0149821 A1 | 6/2009 | Scherson et al. |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 | 6/2010 | Bernstein |
| 2010/0249679 A1 | 9/2010 | Perry et al. |
| 2010/0249680 A1 | 9/2010 | Davis |
| 2011/0009785 A1 | 1/2011 | Meyer et al. |
| 2011/0034861 A1 | 2/2011 | Schaefer |
| 2011/0071447 A1 | 3/2011 | Liu et al. |
| 2011/0082401 A1 | 4/2011 | Iker et al. |
| 2011/0087142 A1 | 4/2011 | Ravikumar et al. |
| 2011/0275983 A1 | 11/2011 | Quisenberry et al. |
| 2011/0282269 A1 | 11/2011 | Quisenberry et al. |
| 2013/0245508 A1 | 9/2013 | Maxon-Maldonado |
| 2013/0245519 A1 | 9/2013 | Edelman et al. |
| 2013/0253383 A1 | 9/2013 | Maxon-Maldonado |
| 2013/0261512 A1 | 10/2013 | Maxon-Maldonado et al. |
| 2014/0012169 A1 | 1/2014 | Wilford et al. |

FOREIGN PATENT DOCUMENTS

| | | |
|---|---|---|
| EP | 0 489 326 | 6/1992 |
| GB | 2373444 A | 9/2002 |
| SU | 689674 | 10/1979 |
| WO | WO-93/09727 | 5/1993 |
| WO | WO-00/40186 | 7/2000 |
| WO | WO-01/14012 A1 | 3/2001 |

OTHER PUBLICATIONS

U.S. Appl. No. 13/962,994, Quisenberry.
U.S. Appl. No. 14/062,428, Quisenberry.
Artikis, T., PCT International Preliminary Report on Patentability as mailed Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 as mailed Apr. 2, 2008, 2 pages.
Young, Lee W., "International Search Report" for PCT/US07/08807 as mailed Mar. 3, 2008, (3 pages).
Mahmoud Karimi Azar Daryany, et al., "Photoinactivation of Escherichia coli and Saccharomyces cerevisiae Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
Quisenberry, Tony, U.S. Appl. No. 13/359,210, filed Jan. 26, 2012.
Quisenberry, Tony, U.S. Appl. No. 29/424,860, filed Jun. 15, 2012.
Quisenberry, Tony, U.S. Appl. No. 13/456,410, filed Apr. 26, 2012.
Copenheaver, Blaine R., "International Search Report" for PCT/US2012/035096 as mailed Aug. 7, 2012, 3 pages.
Quisenberry, Tony, U.S. Appl. No. 13/558,615, filed Jul. 26, 2012.
Copenheaver, Blaine R., "International Search Report" prepared for PCT/US2013/030475 as mailed May 23, 2013, 3 pages.

COMPRESSION SEQUENCED THERMAL THERAPY SYSTEM

CROSS-REFERENCE TO RELATED APPLICATIONS

The present application is a continuation of U.S. patent application Ser. No. 12/730,060, now issued as U.S. Pat. No. 8,753,383, filed Mar. 23, 2010 U.S. patent application Ser. No. 12/730,060 is a divisional application of U.S. patent application Ser. No. 10/894,369, filed Jul. 19, 2004. U.S. patent application Ser. No. 10/894,369 claims the benefit of, and incorporates by reference for any purpose the entire disclosure of, U.S. Provisional Patent Application Nos. 60/488,709 filed Jul. 18, 2003; 60/550,658, filed Mar. 5, 2004; and 60/588,453, filed Jul. 16, 2004. This application incorporates by reference the entire disclosures of U.S. Pat. Nos. 5,097,829; 5,989,285 as well as U.S. patent application Ser. Nos. 12/730,060; 10/894,369; 60/488,709; and 09/328,183, filed Jun. 8, 1998.

BACKGROUND

1. Technical Field

The present invention relates to thermal therapy systems in general, including therapeutic cooling, heating, and compression systems used in association therewith, and more particularly, but not by way of limitation, to a programmable, sequential compression system adapted for high thermal contrast modality, and incorporating multiple, independently controllable chambers in a thermal therapy blanket.

2. Description of the Related Art

Medical care providers have long recognized the need to provide warmth and cooling directly to patients as part of their treatment and therapy. Better recoveries have been reported using cold therapy for orthopedic patients. The benefits of warming patients undergoing surgery has been conclusively proven. It is also desirable to cool portions of a patient's anatomy in certain circumstances. Yet another advantageous therapy is the application of heat then cold to certain areas of injury.

Several devices have been developed that deliver temperature controlled fluids through pads or convective thermal blankets to achieve the above purpose. Typically these devices have a heating or a cooling element, a source for the fluid, a pump for forcing the fluid through the pad or blanket, and a thermal interface between the patient and the temperature controlled fluid. U.S. Pat. No. 4,884,304 to Elkins is directed to a mattress cover device which contains liquid flow channels which provide the selective heating or cooling by conduction.

Devices have also been developed for providing heat to a person in bed. Electric blankets containing electric heating elements have been used for years to warm a person in bed.

Cooling blankets, such as the blanket disclosed in U.S. Pat. No. 4,660,388 to Greene, have also been proposed. Greene discloses a cooling cover having an inflatable pad with plenum chambers at opposite ends thereof. Cool air is generated in a separate unit and directed to the pad and out a number of apertures on the underside of the pad and against the body of the person using the cover.

A disposable heating or cooling blanket is disclosed in U.S. Pat. No. 5,125,238 to Ragan, et al which has three layers of flexible sheeting. Two of the layers form an air chamber and the third includes a comfortable layer for contact with the patient. Conditioned air is directed toward the covered person through a multiplicity of orifices in the bottom layers of the blanket.

A temperature controlled blanket and bedding assembly is disclosed in commonly assigned U.S. Pat. No. 5,989,285 to DeVilbiss et al., the disclosure of which describes a temperature controlled blanket and temperature control bedding system which has the provision of both recirculating temperature controlled fluid and temperature controlled gas to enhance performance for convectively heating or cooling a patient. Counter-flow or co-flow heat exchanging principles between the temperature controlled liquid and the temperature controlled gas achieve temperature uniformity across different sections of the blanket and the bedding system. Drapes and the temperature controlled bedding system provided temperature controlled envelope around a person using the bedding system. In one embodiment of the bedding system, the air portion of the bedding system is provided for use with a patient that supplies the fluid portion of the overall bedding system. In another embodiment of the bedding system, the fluid portion of the bedding system is provided for use with a patient bed which supplies the air portion of the overall bedding system.

U.S. Pat. No. 5,097,829 to Quisenberry describes an improved temperature controlled fluid circulating system for automatically cooling a temperature controlled fluid in a thermal blanket with a thermoelectric cooling device having a cold side and a hot side when powered by electricity. The temperature controlled fluid is cooled by the cold side of the cooling device and pumped through, to, and from the blanket through first and second conduits.

SUMMARY

The present invention relates to a sequential compression blanket for use with heating or cooling therapy. In one aspect, an embodiment of the blanket comprises a plurality of air chambers and a valve assembly. The valve assembly controls the flow of air to each air chamber in order to provide sequential, pulsing, or constant compression to the patient.

In another aspect, one embodiment of the invention includes a compression therapy blanket comprising a plurality of gas, such as air, chambers for receiving a gas to cause compressions, a valve assembly, internal to the compression therapy blanket, for delivering gas to each of the plurality of air chambers in a predetermined pattern, an inlet port for delivering air from a control unit to the valve assemblies, and a plurality of connection for delivering gas from the valve assembly to the plurality of gas/air chambers. The plurality of gas/air chambers may comprise four to seven chambers and an electrical signal connection may be provided for transmitting data related to the predetermined pattern to the valve assembly. One embodiment includes the predetermined pattern comprises sequential inflation of the plurality of chambers to produce series of compression movements peripherally toward the heart of a patient, while another embodiment includes inflating two of the plurality of gas/air chambers simultaneously.

In yet another aspect, the above described compression therapy blanket further comprises a heat transfer fluid bladder for providing temperature therapy to a portion of a patient. The bladder includes a fluid inlet port for delivering heat transfer fluid from the control unit to the heat transfer fluid bladder and a fluid outlet port for delivering heat transfer fluid from the heat transfer fluid bladder to the control unit. The heat transfer fluid bladder delivers thermal therapy to a patient in the form of heat or cold or alternating heat and cold.

In yet another aspect, one embodiment of the invention includes a temperature therapy blanket comprising, a fluid bladder for housing heat transfer fluid, the fluid bladder having a top layer and a bottom layer, a plurality of connections for dispersing the heat transfer fluid throughout the blanket, the plurality of connections connecting the top layer to the bottom layer of the fluid bladder, at least one partition for directing the flow of the heat transfer fluid through the bladder; and means for providing sequenced flows of alternating heat and cold in a high thermal contrast modality to a patient.

In another embodiment of the invention, the above-described temperature therapy blanket further comprises an air bladder disposed outwardly of the fluid bladder in an overlapping relationship therewith for providing select compression therapy, the air bladder having an upper layer and a lower layer and an inlet port for providing air from the control unit to the air bladder.

Yet a further aspect includes one embodiment of the invention comprising a system for passing heat transfer fluid between a control unit and a blanket. The system comprises a reservoir for housing heat transfer fluid for utilization by the system, a flow network in flow communication with the reservoir and including a junction having at least three branches, wherein a first branch receives heat transfer fluid from the reservoir, a second branch receives the heat transfer fluid returning from the blanket, and a third branch for delivering the heat transfer fluid to the blanket, and a pump for creating a low pressure site at the third branch, wherein the low pressure site causes the heat transfer fluid from the second branch to be pulled into the third branch. In one embodiment of the invention, the three-point junction is generally configured as an inverted Y from a fluid flow standpoint.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION

Figure 1:
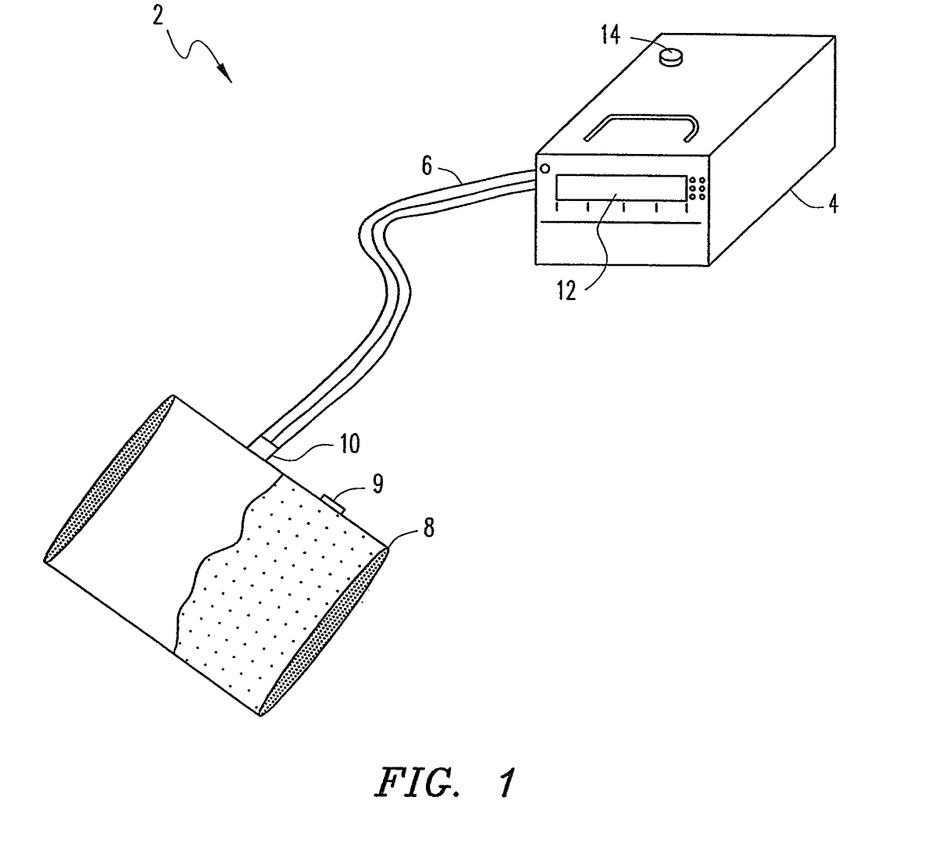
FIG. 1 is an illustration of the patient therapy system according to an embodiment of the present invention.

Referring to FIG. 1, there is shown a patient therapy system 2 according to the principles of the present invention. The patient therapy system 2 comprises a control unit 4, a blanket 8, and a connector 10. The blanket 8 further comprises an emergency relief valve 9. In operation, a heat transfer fluid is deposited in the control unit 4 via an aperture 14. The heat transfer fluid is cooled or heated by the control unit 4 and pumped to the blanket 8 by connector tubes 6. The heat transfer fluid flows into the blanket 8 through an inlet port, and exits through an outlet port to the control unit 4 via the connector 10 and connector tubes 6. Similarly, a gas may be pumped by the control unit 4 to the blanket 8 through the connector tubes 6 and the connector 10 to provide compression therapy. In addition, additional connector tubes 6 may be present to allow for both heat transfer fluid and gas to be passed to the blanket for simultaneous temperature therapy and compression therapy.

The control unit 4 receives data and manipulates any one of a plurality of therapeutic characteristics of the blanket 8 based on the data. The blanket 8 is adapted for the administration of hot, cold, and/or compression therapies to a body portion of the patient. For example, the blanket 8 may extend from the fingertips to the shoulder, the toes to the hip, or various other configurations. Current thermal design requirements for temperature therapy in accordance with one embodiment of the present invention are as follows: 1) the system must be able to heat the fluid from around 49° F. to around 105° F. with the largest blanket attached to a typical man at an ambient of 77° F. within 10 minutes, 2) the system must be able to cool the fluid from 105° F. to 49° F. with the largest blanket attached to a typical man at an ambient of 77° F. within 20 minutes, and 3) the system must cool the fluid to 37° F. at an ambient of 77° F. within 90 minutes. These requirements should be with a minimum compression of 25 mm Hg. In addition, according to some embodiments, the blanket 8 may diffuse oxygen into the portion of the body. The connector 10 provides a fluid and/or gas connection between the control unit 4 and the blanket 8 for the transfer of gas and heat transfer fluid. The connector 10 may also allow for transfer of electrical sensor signals and/or data signals between the blanket 8 and the control unit 4. The emergency relief valve 9 is utilized to quickly decompress the blanket 8 if needed.

Figure 2:
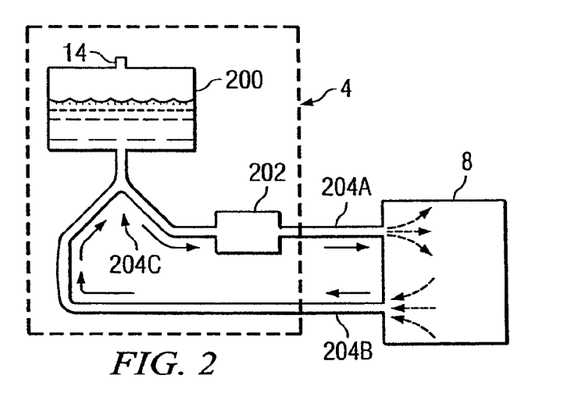
FIG. 2 is a block diagram illustrating the flow of heat transfer fluid according to an embodiment of the present invention.

Referring now to FIG. 2, a block diagram of one embodiment of the flow of heat transfer fluid between the control unit 4 and the blanket 8 is illustrated. The control unit 4 includes a heat transfer fluid reservoir 200 and at least one heat transfer assembly (HTA) 202 for heating and/or cooling the heat transfer fluid. Before the blanket 8 is utilized for temperature therapy, the system is primed with the heat transfer fluid. When the system is primed, substantially no air exists in the tubes 204 between the reservoir 200, HTA 202, and blanket 8. The flow tubes in the control unit 4 between the reservoir 200, HTA 202, and blanket 8 form a three-point junction 204C. In the preferred embodiment, the three-point junction 204C is formed as an inverted Y, however, other shapes and orientations are possible. By utilizing a three-point junction 204C, the heat transfer fluid returning from the blanket 8 is recirculated to the HTA 202 without utilizing heat transfer fluid from the reservoir 200. The three-point junction 204C allows the HTA 202 to heat or cool the heat transfer fluid that has already been heated or cooled prior to entering the blanket 8. In the preferred embodiment, the HTA 202 does not heat or cool the entire contents of the reservoir 200, but merely the portion of the heat transfer fluid that is currently circulating through the blanket 8 and tubing 204. In essence, the reservoir is generally "by-passed" unless more fluid volume is needed. In the three-point junction 204C, heat transfer fluid returning from the blanket 8 may be pulled, via a pump, to the HTA 202. If more heat transfer fluid than that which is already circulating through the system is required, then the heat transfer fluid from the reservoir is introduced into the system.

Figure 3:
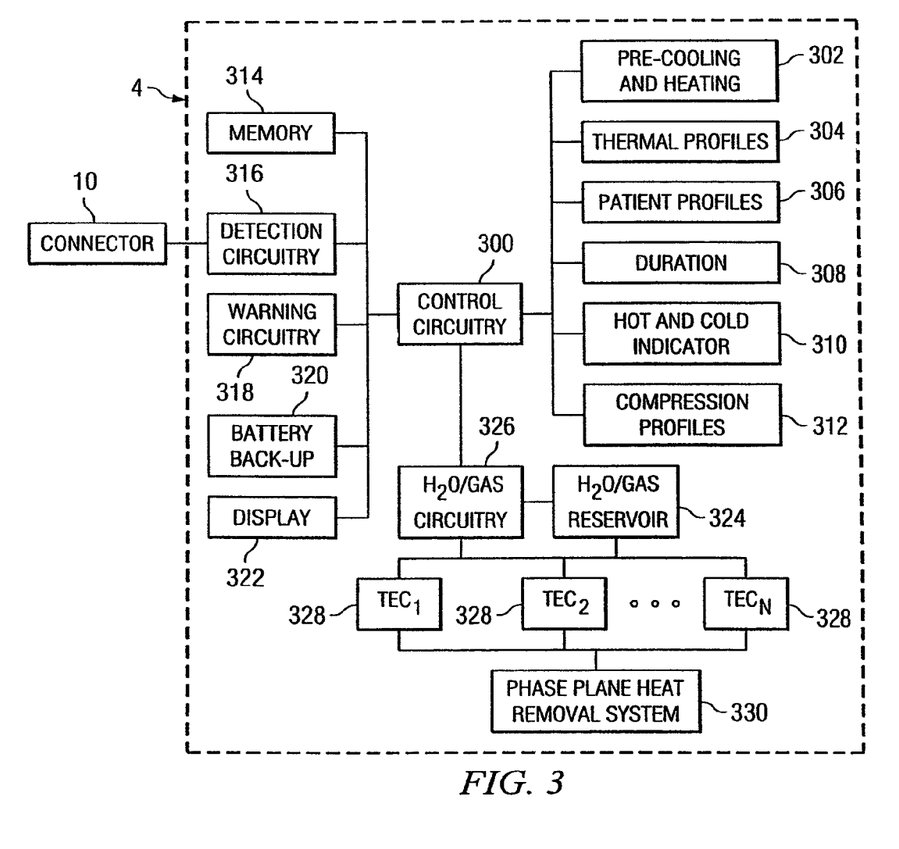
FIG. 3 is a block diagram of the control circuitry according to an embodiment of the present invention.

Referring now to FIG. 3, and more specifically to the control unit 4, control circuitry 300 according to an embodiment of the present invention is illustrated. The control circuitry 300 is coupled to pre-cooling and pre-heating circuitry 302, thermal profile circuitry 304, patient profile circuitry 306, time duration circuitry 308, hot and cold indicator circuitry 310, and compression profile circuitry 312. The control circuitry 300 is further coupled to a memory 314, detection circuitry 316, warning circuitry 318, and a backup battery 320. A display 322 is provided for displaying the output of the control circuitry 300 and for the input of data to control various therapeutic values of the blanket 8. A dual water and gas reservoir 324 having water and gas reservoir circuitry 326 is further coupled to the control circuitry 300. Reservoir circuitry 326 is coupled both to the control circuitry 300 and to a plurality of thermal electric coolers 328. The thermal electric coolers 328 heat and/or cool the heat transfer fluid contained within the fluid/gas reservoir 324. Coupled to the thermal electric coolers 328, there is shown a phase plane heat removal system 330.

Coupled to the control circuitry 300 is the pre-cooling and pre-heating circuitry 302 which heats and/or cools the temperature of the heat transfer fluid prior to the application of the blanket 8 to the patient. Thermal profile circuitry 304, patient profile circuitry 306, and compression profile circuitry 312 allow the user of the patient therapy system 2 to apply compression and/or thermal therapy to a patient according to preset values which depend on the type of injury and physical attributes of the patient. Exemplary attributes of the patient, thermal, and/or compression profiles are illustrated in Table 1 below.

TABLE 1

| Patient Record | Bytes | Type |
| --- | --- | --- |
| RTC Year | 1 | character |
| RTC Month | 1 | character |
| RTC Day | 1 | character |
| RTC Hour | 1 | character |
| RTC Minute | 1 | character |
| Coolant Set Temp | 2 | signed integer |
| Coolant Temp | 2 | signed integer |
| Compression Set | 1 | unsigned character |
| Compression Reading | 2 | unsigned integer |
| Therapy Mode | 1 | bit |
| Compression Switch Status | 2 | bits |
| Control Mode | 3 | bits |
| Alarms | 1 | bit |

As illustrated in Table 1, a record of the actual use of the temperature therapy blanket may be recorded by the Year, Month, Day, Hour, and Minute attributes. The temperature therapy settings and compression settings may also be stored via the Coolant Set Temp and Compression Set attributes. The actual temperature and compression may be stored via the Coolant Temp and Compression Reading attributes. The particular therapy mode chosen is assigned to the Therapy Mode attribute. For example, the patient may wish to apply cooling therapy without compression, heat therapy without compression, contrast therapy without compression, cooling therapy with compression, heat therapy with compression, contrast therapy with compression, or compression without temperature therapy. The profiles and usage data may also be sent to a computer or printed for medical records, etc.

The detection circuitry 316 is coupled to the control circuitry 300 and to the connector 10 of FIG. 1 to alert the user of whether the connector 10 is properly or improperly connected to the blanket 8. A disconnect signal may be sent to the control circuitry 300 to warn the user of a problem with the connector 10. The battery backup 320 supplies power to the control unit 4 during periods when an AC current is not available. The control circuitry 300 may also forward data related to specifics of the temperature and compression therapy to the display 322. The display 322 may display indicators related to the data from the control circuitry 300 and/or other portions of the system 2.

The control circuitry 300, in conjunction with the memory 314, thermal profile circuitry 304, patient profile circuitry 306, time duration circuitry 308, and compression profile circuitry 312 provides cooling and heating therapy with a programmable set point between 37 and 66° F. and 90 and 105° F. The control circuitry 300 allows for contrast therapy programmable for alternating between cooling for a predetermined time interval and heating for a predetermined time interval, or constant therapy for only heating or only cooling for a predetermined time interval. The control circuitry 300 also allows for compression therapy separate from, or in conjunction with, the contrast or constant thermal therapy. Compression therapy enhances thermal contact for more efficient thermal transfer with the tissue under therapy. The compression therapy may also provide pulse compression by alternating between a plurality of chosen pressure levels to gently, but firmly pulse massage the tissue. Compression therapy that sequentially compresses a portion of the patient under therapy may also be initiated from the control circuitry 300. Further, the control circuitry 300, in conjunction with the memory 314, may provide optional electronic recording of therapy patient identification and chosen thermal, contrast, constant, compression, and/or oxygen treatment levels applied with time indicators and duration indicators of each treatment mode as noted above with respect to Table 1. The patient may optionally readout, print, and/or electronically retain the therapy patient record within the memory 50. Moreover, the control circuitry 300 may provide a bio-impedance measurement to estimate the total body water content to assess hydration conditions. Also, an exemplary embodiment of the patient therapy system 2 of FIG. 1 may provide electronic muscle stimulation to accelerate return of muscle condition to normal.

Figure 4A:
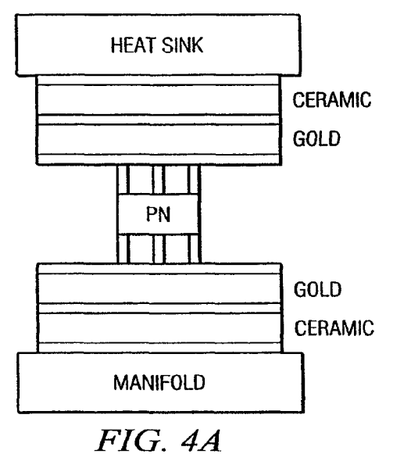
FIGS. 4A-4C are block diagrams of thermoelectric device assemblies according to embodiments of the present invention.

Referring now to FIG. 4A, there is shown a diagrammatic schematic of one embodiment of an improved thermoelectric device assembly in accordance with one embodiment of the principles of the present invention. The TEC of this particular embodiment incorporates a layer of gold that interfaces with the ceramic. This particular interface affords the necessary strength to connect the ceramic directly to the billets for a high thermal contrast modality in accordance with certain aspects of the present invention. With such a design, a much higher thermal contrast modality and thermal cycle capability is achieved. Moreover, it has been suggested by Applicants herein that with such an assembly, approximately 100,000 heating and cooling cycles may be possible in the high thermal contrast modality. The present embodiment affords an arrangement of the appropriate TEC interface materials with the heat exchanger to optimize the ability to accept high thermal contrast through thousands of cycles manifesting extreme expansion and contraction as is inherent in high contrast thermal systems. The utilization of thermal grease between the TEC and the heat sink and manifold is currently contemplated. It has further been recognized that the layer of gold appears to reduce the stress on the solder joints within the TEC. A more robust connection is thus afforded between the ceramic and the other elements inside the TEC. It has further been recognized that the use of thermal grease instead of plastics and the like is preferable in at least one embodiment of the present invention.

Figure 4B:
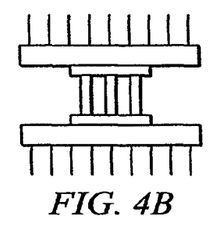

Referring now to FIG. 4B, a diagrammatic schematic illustrates thermal cycling with the TEC capable of withstanding the stresses of thermal cycling. The TEC is capable of withstanding the stresses of thermal cycling during normal operation at the following conditions: 150 PSI loading, ΔT in the cooling mode, cool side=15° C.; hot side=60° C. With such an embodiment, the following performance matrix may be realized: Thermal characteristics: $Q_{max} \geq 52$ Watts at 25° C.

Figure 4C:
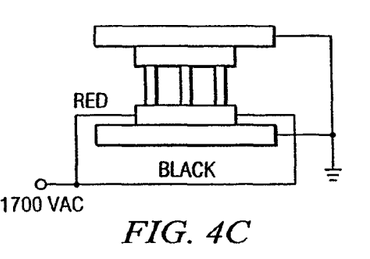

Referring now to FIG. 4C, physical characteristics of one embodiment of the present invention are illustrated. The leads and perimeter of the TEC must be sealed with a sealant that will meet the following: AC Hipot of 1700 VAC for 1 minute with the TEC's sandwiched between two ground planes and a leakage requirement of ≤10 mA at 1700 VAC. It is preferable for the sealants used for the leads and the perimeter to be of similar materials.

Figure 5A:
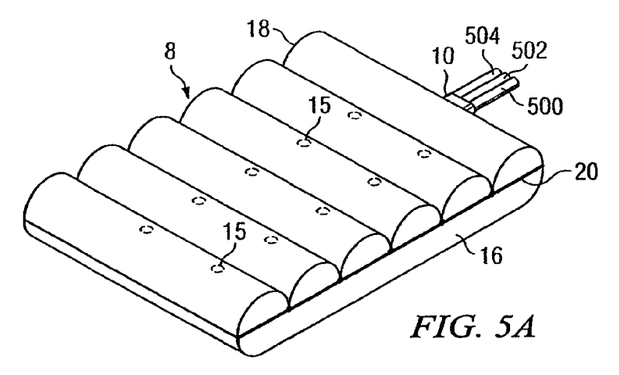
FIGS. 5A-5B are illustrations of a cross-sectional view of the blanket portion of the patient therapy system according to an embodiment of the present invention.

Referring now to FIG. 5A, there is shown the connector 10 of FIG. 1 connected to the therapy blanket 8. A plurality of connections 15 extend throughout the interior of the fluid bladder of blanket 8 so as to avoid all concentration of fluid in one portion of the therapy blanket 8. Layer 18 is a layer of a gas/fluid impermeable material and layer 20 is a second layer of gas/fluid impermeable material. A first bladder, defined by layers 18 and 20, contains heat transfer fluid from the water/gas reservoir 324 (via tubes 500 and 502) while the second bladder, which is defined by layers 20 and 16, receives gas (via tube 504). A single connection 15 is formed by sealing layers 18 and 20 one to another. Layers 16, 18, and 20 are sealed one to another along their periphery.

Figure 5B:
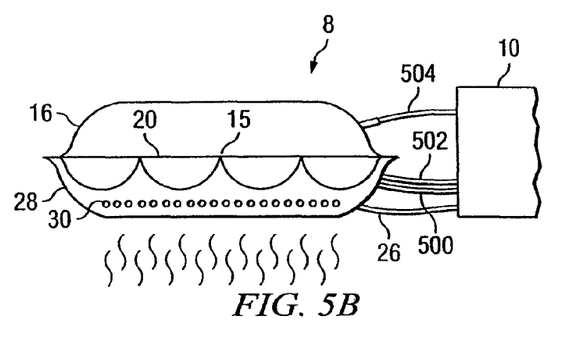

In an exemplary embodiment shown in FIG. 5B, gas permeable layer 28 is coupled beneath the gas bladder and fluid bladder of FIG. 5A. Layer 28 may be sealed contiguous with the periphery of the gas bladder and fluid bladder of FIG. 5A. A tube 26 injects oxygen into the gas permeable layer 28 for diffusion along a surface of the patient via a series of diffusion holes 30 formed in layer 28. One method of providing oxygen to an injured portion of a patient is described in the aforementioned U.S. Pat. No. 5,989,285 to DeVilbiss et al.

Figure 5C:
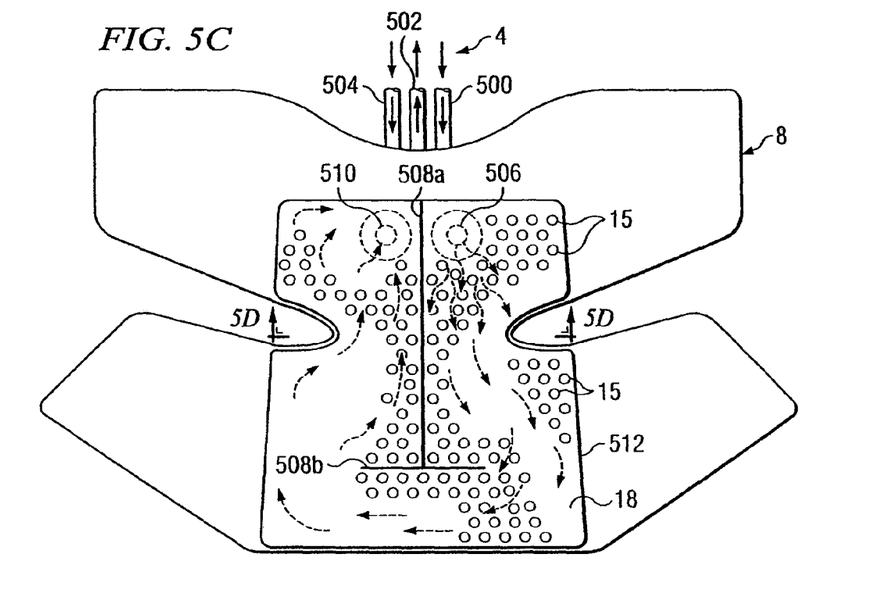
FIG. 5C is an illustration of a bottom view of the blanket in accordance with an embodiment of the present invention.

Referring now to FIG. 5C, a temperature therapy blanket 8 having a pre-selected shape and compression capabilities is illustrated. The underside of the blanket 8 (shown) is placed directly against a portion of the patient. The fluid bladder is thus adjacent the patient. Heat transfer fluid flows into the blanket 8 from inlet hose 500 and heat transfer fluid flows out of the blanket via outlet hose 502. A gas, for compression, flows into the blanket 8 from air inlet hose 504. The air inlet hose 504 may also be utilized to provide oxygen for oxygenation purposes. Alternatively, oxygenation gas may be provided by a separate hose. Heat transfer fluid travels through the inlet hose 500, through fluid inlet port 506, and into the blanket 8. The connections 15 allow the heat transfer fluid to evenly disperse throughout the fluid bladder. Partitions 508a, 508b control the flow of heat transfer fluid throughout the fluid bladder. Partition 508a prevents heat transfer fluid from entering the blanket 8 at the inlet port 506 and immediately exiting the blanket via outlet port 510. Partition 508a forces the heat transfer fluid to travel towards the end of the blanket 8 remote from the inlet port 506. Partition 508b, in conjunction with connections 15, causes the heat transfer fluid to travel across the width of the blanket 8. The edges of the fluid bladder are joined to the edges of the air bladder at seal 512. The heat transfer fluid may then exit the blanket 8 at the outlet port 510. The travel of the heat transfer fluid is indicated by arrows in FIGS. 5C and 5D.

Figure 5D:
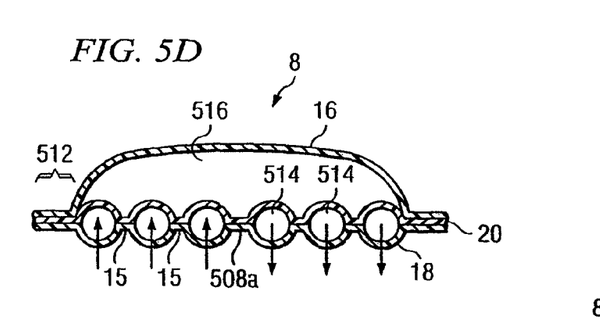
FIG. 5D is an illustration of a cross-sectional view of the blanket of FIG. 5C in an inverted position relative to FIG. 5C.

Referring now to FIG. 5D, the blanket 8 is turned over relative to FIG. 5C and a cross-sectional view along line A-A of FIG. 5C is illustrated. As described above, the fluid bladder 514 (disposed against the patient) and air bladder 516 are joined together at seal 512. Connections 15 join the upper layer and lower layer of the fluid bladder 514 together. The partition 508a segregates the heat transfer fluid from the inlet port 506, illustrated by the downward arrows, from the heat transfer fluid flowing to the outlet port, illustrated by the upward arrows. The air bladder 516 is oriented over the fluid bladder 514 to press the fluid bladder 514 against a portion of the patient (not shown in this view).

Figure 6A:
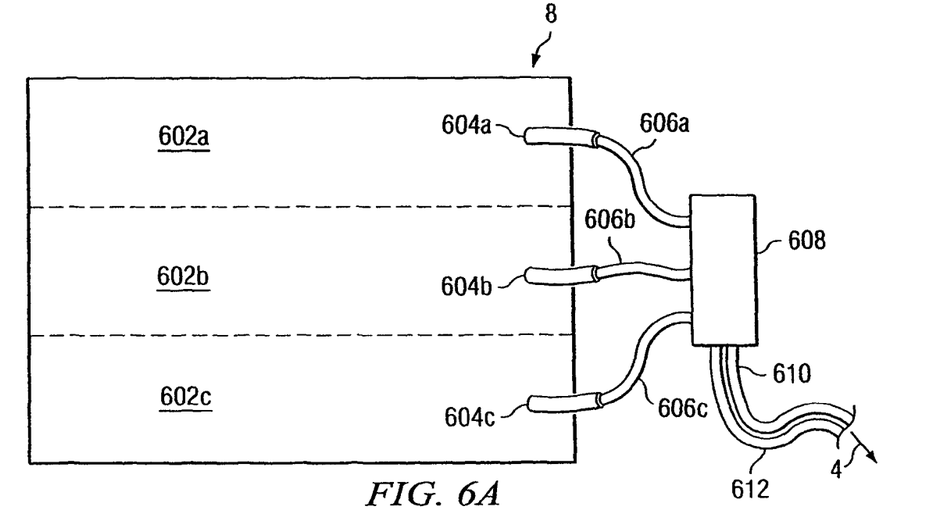
FIG. 6A is an illustration of the valve assembly and sequential compression blanket in accordance with one embodiment of the present invention.

Referring now to FIG. 6A, a sequential compression blanket 8 in accordance with an embodiment of the present invention is illustrated. The sequential compression blanket 8 may also include temperature therapy as illustrated above, or the sequential compression blanket 8 may be a stand alone blanket that may be applied directly to a surface of a patient or over a temperature therapy blanket. The sequential compression blanket 8 includes a plurality of air chambers 602 with inlet lines 604 for each air chamber 602. In the preferred embodiment, the blanket 8 includes four to seven air chambers 602, although more or fewer air chambers 602 may be utilized in accordance with embodiments of the present invention. Tubing 606 connects the inlet lines 604 to a valve assembly 608 that is separate from both the blanket 8 and the control unit 4. Additional tubing 610 connects the valve assembly 608 to the control unit 4. The valve assembly 608 operates to control the flow of air to each chamber 602 via valves (not shown) that allow air flow to the tubing 606 for each air chamber 602. The valve assembly 608 may operate to provide sequential compression in a first direction by first filling and releasing air chamber 602a, next filling and releasing air chamber 602b, and lastly filling and releasing air chamber 602c. The valve assembly 608 may operate to provide sequential compression in the opposite direction by first filling and releasing air chamber 604c, next filling and releasing air chamber 604b, and lastly filling and releasing air chamber 604a. Alternatively, the valve assembly 608 may provide pulsing compression by substantially simultaneously filling the air chambers 602 and, a predetermined time interval later, releasing the air chambers 602. Although the above embodiment illustrates specific sequential and pulsing compression techniques, it will be understood by one skilled in the art that numerous compression techniques may be utilized without departing from aspects of the present invention. For example, multiple air chambers 602 may be filled simultaneously or compression could be applied by first filling air chamber 602a, next filling air chamber 602b, lastly filling air chamber 602c, and releasing the air chambers 602 substantially simultaneously. In various embodiments, the air chambers 602 are sequenced to provide movement peripherally toward the heart.

The valve assembly 608 receives sequencing instructions from an electrical line 612 that connects to the control unit 4. The electrical line 612 may also provide for communication of other data, such as sensor data or oxygenation data, between the blanket 8 and the control unit 4. For example, the blanket 8 may include temperature sensors to determine the temperature of the heat transfer fluid within the blanket 8. The sensor data is then transmitted to the control unit 4, via the electrical line 612, so that the control unit 4 may adjust the cooling or heating of the heat transfer fluid as necessary.

Figure 6B:
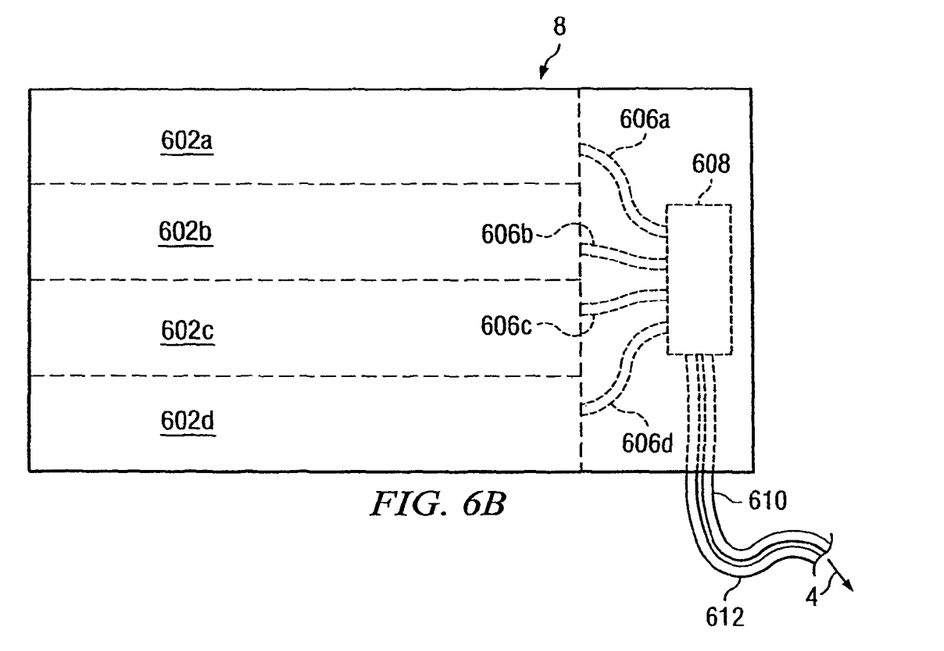
FIG. 6B is an illustration of the valve assembly and sequential compression blanket in accordance with an alternate embodiment of the present invention.

Referring now to FIG. 6B, an alternate embodiment of the present invention is illustrated. This embodiment includes a valve assembly 608 that is internal to the sequential compression blanket 8 and four air chambers 602 within the sequential compression blanket 8, although the amount of air chambers may vary from blanket to blanket. The valve assembly 608 functions in a manner similar to the valve assembly 608 of FIG. 6A except that an additional valve is provided for the fourth air chamber 602*d* and tubing 606*d*. The valve assembly 608 and tubing 606 are internal to the sequential compression blanket 8. Therefore, the only item visible to a patient is the tubing 610 that exits the sequential compression blanket 8 and connects to the control unit 4. Although the sequential compression blanket 8 has been illustrated as a substantially rectangular blanket, it will be understood by one skilled in the art that the blanket 8 may be formed in any shape to conform to any portion of a patient's body, such as a shoulder, wrist, foot, neck, back, etc.

Figure 6C:
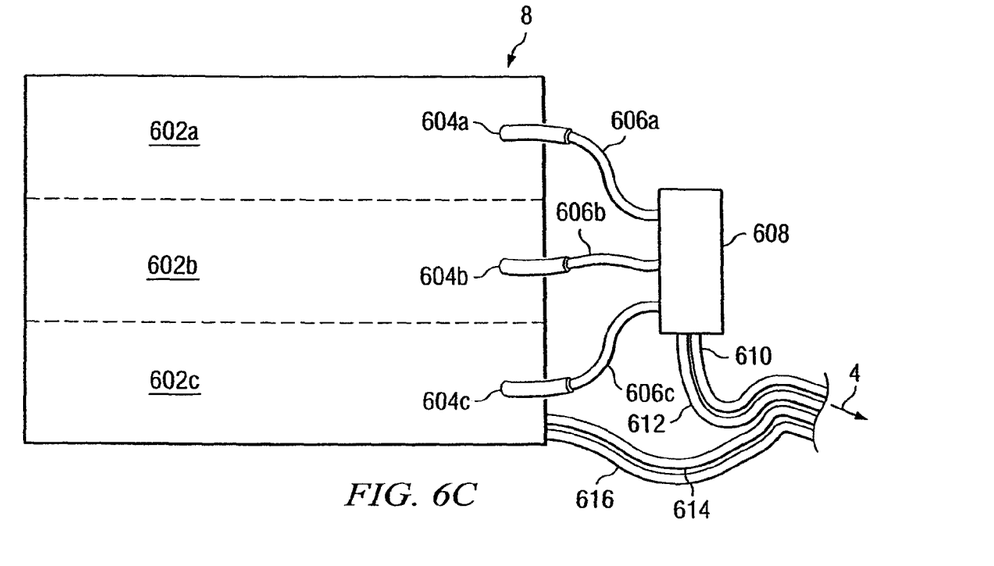
FIG. 6C is an illustration of the valve assembly of FIG. 6A according to an alternate embodiment of the present invention.
Figure 6D:
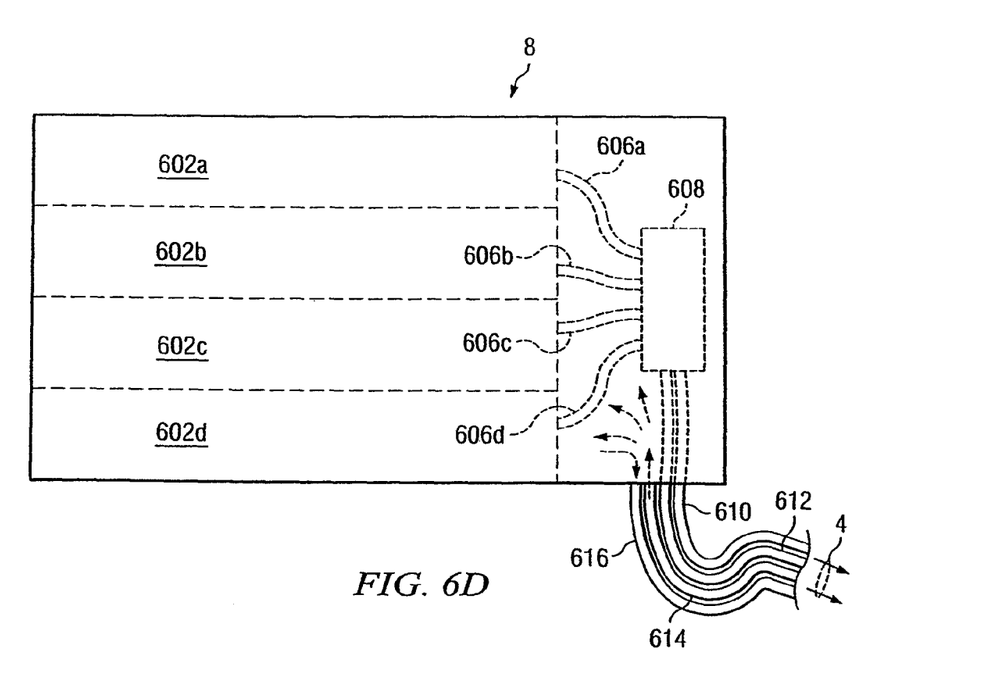
FIG. 6D is an illustration of the valve assembly of FIG. 6B according to an alternate embodiment of the present invention.
Figure 7A:
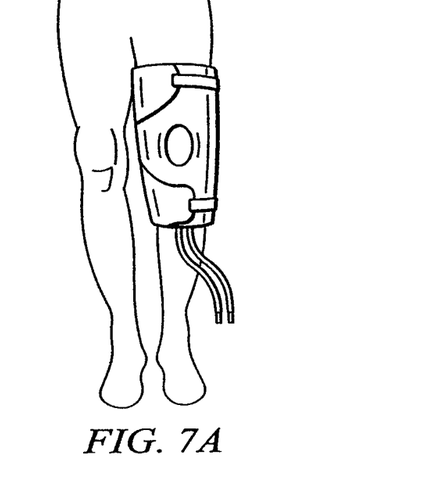
FIGS. 7A-7I are illustrations of several exemplary embodiments of the patient therapy system of the present invention.
Figure 7B:
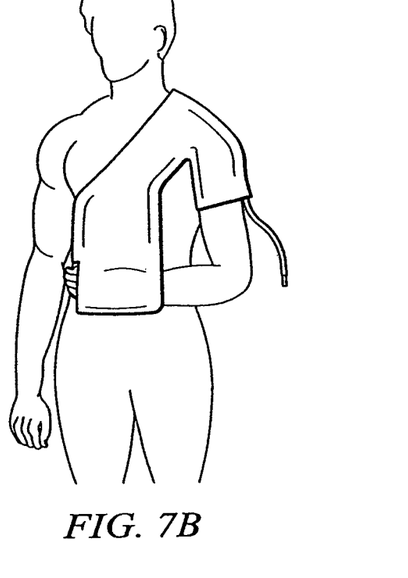
Figure 7C:
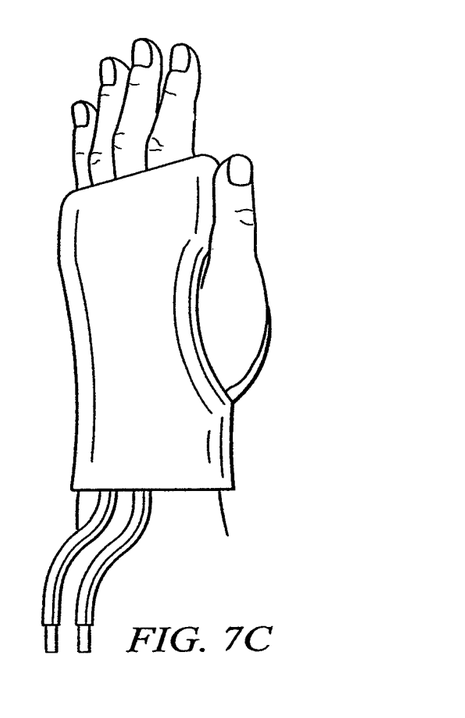
Figure 7D:
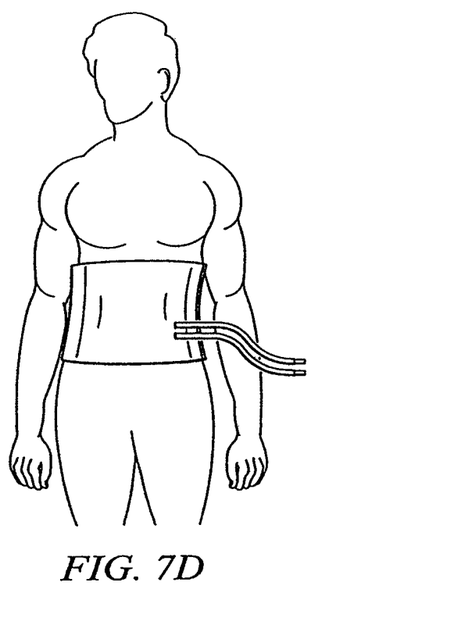
Figure 7E:
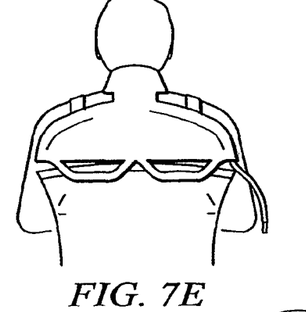
Figure 7F:
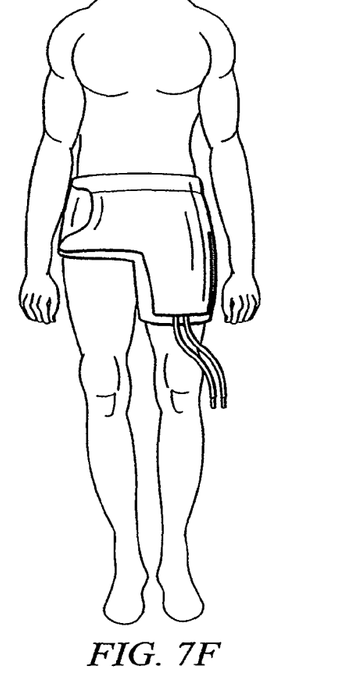
Figure 7G:
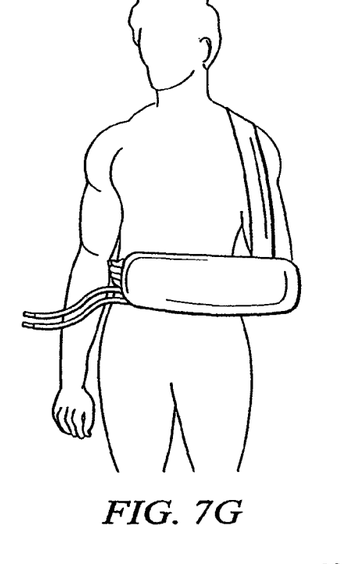
Figure 7H:
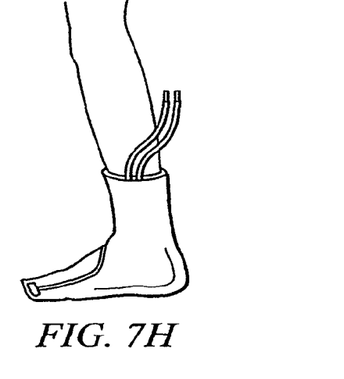
Figure 7I:
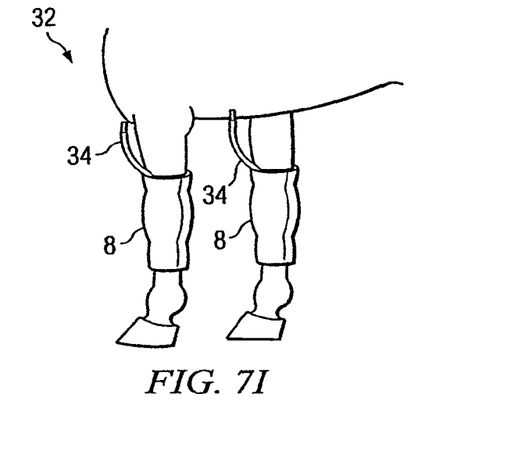

Referring now to FIGS. 6C-6D, alternate embodiments of the sequential compression blanket 8 is illustrated. The blanket as shown also includes a fluid bladder with an inlet fluid tube 614 and outlet fluid tube 616. The compression functions similarly to that described in FIGS. 6A and 6B except that the compression bladder presses the fluid bladder onto a portion of the patient. The fluid bladder may be similar to that illustrated in FIGS. 5A-5D, although other configurations of fluid bladders may be utilized in conjunction with the compression blanket of embodiments of the present invention.

Referring now to FIGS. 7A-7I, various configurations of the blanket 8 adaptable to various portions of a patient body are illustrated. Although the blankets 8 are illustrated with a specific configuration of tubing, connectors, fasteners, etc., it will be understood by one skilled in the art that other configurations may be utilized in accordance with embodiments of the present invention.

Figure 8:
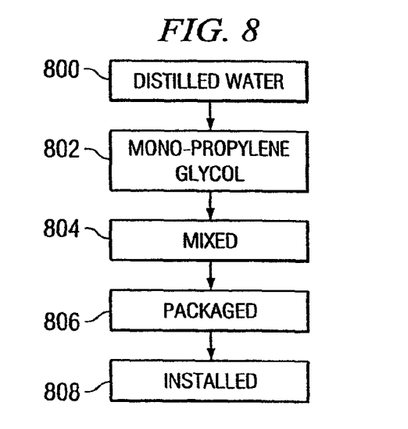
FIG. 8 is an illustration of a method of creating and packaging a heat transfer fluid utilized according to an embodiment of the present invention.

Referring now to FIG. 8, a method of creating and packaging a heat transfer fluid according to an embodiment of the present invention is illustrated. Although the heat transfer fluid described below may be utilized with the present invention, other heat transfer fluids may also be utilized in conjunction with the system of the present invention. In the preferred embodiment, the heat transfer fluid incorporates water with propylene glycol. A 15% solution of propylene glycol with distilled water is suggested to reduce the freezing set point within the heat transfer fluid and to eliminate the accumulation of bacteria. At step 800, distilled water is provided. At step 802, monopropylene glycol is provided and is mixed with the water at step 804. The distilled water and monopropylene glycol may be mixed in a ratio of about 15% monopropylene glycol and 85% distilled water. The mixture is packaged at step 806 and installed at step 808.

The previous description is of a preferred embodiment for implementing the invention, and the scope of the invention should not necessarily be limited by this description. The scope of the present invention is instead defined by the following claims.

What is claimed is:

1. A method for contiguously providing compression therapy and thermal therapy to a patient, the method comprising:
   providing a blanket having a fluid bladder and a plurality of air chambers;
   securing the blanket around an appendage of a patient such that the fluid bladder is in thermal contact with the appendage and the plurality of air chambers are disposed outwardly of the fluid bladder relative to the appendage;
   compressing the fluid bladder against the appendage at a first pressure when the plurality of air chambers are deflated;
   thermally conditioning a heat-transfer fluid to a predetermined temperature using one or more thermoelectric coolers;
   flowing the heat-transfer fluid through the fluid bladder to provide thermal therapy to the patient; and
   selectively inflating and deflating each of the plurality of air chambers in a predetermined pattern to compress selective portions of the fluid bladder against the appendage at a second pressure greater than the first pressure while the thermally conditioned heat-transfer fluid is flowed therethrough.

2. The method of claim 1, and further comprising repeating the selectively inflating and deflating to provide sequenced compression to the patient.

3. The method of claim 1, wherein the selectively inflating and deflating comprises providing compressed gas to the plurality of air chambers in a predetermined pattern.

4. The method of claim 1, wherein the selectively inflating and deflating comprises providing compressed gas to a first air chamber for a first predetermined time period before providing the compressed gas to a second air chamber for a second predetermined time period.

5. The method of claim 4, comprising providing the compressed gas to a third air chamber for a third predetermined time period after providing the compressed gas to the second air chamber for the second predetermined time period.

6. The method of claim 4, comprising providing the compressed gas to the first air chamber after providing the compressed gas to the third air chamber.

7. The method of claim 4, comprising releasing the compressed gas from the first air chamber before providing the compressed gas to the second air chamber.

8. The method of claim 4, comprising releasing the compressed gas from the first air chamber after providing the compressed gas to the second air chamber.

* * * * *